US009867558B2

(12) United States Patent
Rabischong et al.

(10) Patent No.: US 9,867,558 B2
(45) Date of Patent: Jan. 16, 2018

(54) METHOD AND APPARATUS FOR ASSESSING PROPRIOCEPTIVE STATUS FOR AT LEAST ONE JOINT OF A PERSON

(71) Applicants: CENTRE NATIONAL DE LA RECHERCHE SCIENTIFIQUE, Paris (FR); UNIVERSITE D'AIX MARSEILLE, Marseilles (FR); ASSISTANCE PUBLIQUE DES HOPITAUX DE MARSEILLE, Marseilles (FR)

(72) Inventors: Pascale Rabischong, Marseilles (FR); Patrick Sainton, Marseilles (FR); Violaine Sevrez, Lyons (FR); Joël Coste, Marseilles (FR)

(73) Assignees: CENTRE NATIONAL DE LA RECHERCHE SCIENTIFIQUE, Paris (FR); UNIVERSITE D'AIX MARSEILLE, Marseilles (FR); ASSISTANCE PUBLIQUE DES HOPITAUX DE MARSELLE, Marseilles (FR)

( * ) Notice: Subject to any disclaimer, the term of this patent is extended or adjusted under 35 U.S.C. 154(b) by 0 days.

(21) Appl. No.: 14/655,113

(22) PCT Filed: Dec. 30, 2013

(86) PCT No.: PCT/IB2013/003206
§ 371 (c)(1),
(2) Date: Jun. 24, 2015

(87) PCT Pub. No.: WO2014/102617
PCT Pub. Date: Jul. 3, 2014

(65) Prior Publication Data
US 2015/0342517 A1 Dec. 3, 2015

(30) Foreign Application Priority Data

Dec. 31, 2012 (FR) .................................. 12 290463

(51) Int. Cl.
*A61B 5/00* (2006.01)
*A61B 5/11* (2006.01)

(52) U.S. Cl.
CPC .......... *A61B 5/1121* (2013.01); *A61B 5/1124* (2013.01); *A61B 5/4519* (2013.01); *A61B 5/4528* (2013.01); *A61B 5/4538* (2013.01)

(58) Field of Classification Search
CPC ... A61B 5/1121; A61B 5/1122; A61B 5/1124; A61B 5/1126; A61B 5/11; A61B 5/4519; A61B 5/4528; A61B 5/4538
See application file for complete search history.

(56) References Cited

U.S. PATENT DOCUMENTS 6,155,993 A 12/2000 Scott
8,827,718 B2 * 9/2014 Chiu .................... A61B 5/1071
434/258

(Continued)

FOREIGN PATENT DOCUMENTS

WO 2008/052349 A1 5/2008

OTHER PUBLICATIONS

International Search Report dated May 23, 2014, issued in corresponding application No. PCT/IB2013/003206 (5 pages).

(Continued)

*Primary Examiner* — Max Hindenburg
(74) *Attorney, Agent, or Firm* — Westerman, Hattori, Daniels & Adrian, LLP (57) ABSTRACT

The present invention relates to a method of assessing proprioceptive status by calculating a proprioceptive score Sp from absolute and variable errors between target angles and angles estimated and joint motion detection by the person tested, and/or between measured time of perceived movement of the joint of the tested person these proprio- (Continued)

ceptive scores of a person being associated with an assessment date and then stored with a date so as to serve as a reference when said person is monitored or when there is a comparison of said person with at least another person. The present invention also concerns an apparatus for the proprioceptive assessment of at least one joint, this apparatus having two movable parts (8, 9) with drive means (12, 15) particular for the pivoting of the movable parts (8, 9), means of determining the pivot angle for each of the first and second parts (8, 9) also being provided. Applications are in the field of proprioceptive assessment by movement of a limb of a person.

20 Claims, 6 Drawing Sheets

(56) References Cited

U.S. PATENT DOCUMENTS

| | | | |
|---|---|---|---|
| 8,834,169 B2 * | 9/2014 | Reinkensmeyer ... | A61H 1/0274 434/247 |
| 8,840,570 B2 * | 9/2014 | Branch ................ | A61B 5/1121 600/587 |
| 9,597,015 B2 * | 3/2017 | McNames ............ | A61B 5/1121 |
| 2008/0108883 A1 | 5/2008 | Scott et al. | |

OTHER PUBLICATIONS

Lönn et al., "Reliability of position sense testing assessed with a fully automated system", Clinical Physiology, Jan. 1, 2000, pp. 30-37, vol. 20, No. 1, cited in the ISR.

\* cited by examiner

METHOD AND APPARATUS FOR ASSESSING PROPRIOCEPTIVE STATUS FOR AT LEAST ONE JOINT OF A PERSON

The present invention relates to a method and apparatus for assessing the proprioceptive status for at least one joint of a person in stataesthesia and/or in kinaesthesia.

Proprioception refers to an ability of a person to sense, without any visual information, the orientation of its different body segments with respect one to another. As such proprioception is a "sixth sense" which encompasses two main modalities: stataesthesia and kinaesthesia. These modalities correspond to the ability of a person to perceive the position and the movement of his/her segments in space, respectively.

Stataesthesia is mostly assessed by mean of matching tests that evaluate the ability of the person to accurately reproduce a specific joint angle. Such tests always comprise two stages: a first during which the assessed joint is placed in a predetermined position referred to as the target position; and a second during which the person attempts to reproduce the position. In spite of this shared two stages methodology, matching tests may largely vary. Positioning and repositioning can for example be performed actively (by the person him/herself), passively (by an experimenter or a dynamometer for example) or externally (a representation of the body is used). The target position may be maintained between 3 and 10 seconds, for example, as the choice on the amount of time is based on a compromise between being sufficient for the person being assessed to be able to memorise the target position and being short enough in order to avoid generating muscular fatigue. The target angle as well as the initial angle, the direction of displacement and the velocity can vary as well. Regarding kinaesthesia, the assessment is mostly performed by tests that evaluate the ability of the person to detect a passive movement at the joint being assessed. To this aim, the segment is passively moved at a constant and very slow speed of 0.5° to 2°/sec until the person signals that a limb movement occurred. A threshold to detection of passive movement is thus registered in terms of either angular motion or time span between the initiation of movement and its detection by the person.

Apparatus for assessing proprioception are known from the prior art. For example, the document WO-A-2008/052349 describes an apparatus comprising two articulated elements that can be attached to one of the limbs of the person being tested. This apparatus supplies data concerning the geometry and/or placement and/or movement of each limb in a two-dimensional or three-dimensional space.

The main drawback of existing devices for assessing proprioceptive status lies in the fact that they are designed to be used by scientists. That implies a thorough knowledge of the experimental protocol to be operated.

The results for stataesthesia or kinaesthesia tests carried-out with such devices are given in the form of raw angular values that remain to be interpreted in connection with the particular experimental condition used. Thus, these results are not understandable for the ordinary man and, the experimenter in charge of the assessment must have specific abilities to process and interpret them. Besides, installing the person being tested and taking measurements is often time consuming.

Furthermore, those experimental devices allow evaluation of only one of the modality of the proprioceptive sense and for one single joint. For example, they would allow for evaluation of kinaesthesia only and just for the knee joint.

Also, the currently existing proprioceptive assessment apparatus does not provide sufficient comfort for the person for whom at least one joint is being tested. Indeed, relaxation of the person is fundamental in order to ensure validity of the measurements. Otherwise, the results may be distorted.

The aim of the present invention is to solve the main drawbacks mentioned above.

To this end, in accordance with a first aspect, the invention concerns a method of assessing the proprioceptive status for at least one joint of a person being tested, this status being assessed in stataesthesia and/or in kinaesthesia, which comprises:

a step of imposing a pivoting movement on the joint of the person being tested, in kinaesthesia, followed by a step of indication by the person that the movement has been perceived or stopped, and/or, in stataesthesia, after stopping the movement imposed when a predetermined target value of at least one parameter of the movement has been reached, followed by a step of reproduction of the movement by the person, a step of measuring an estimated value of the parameter of the movement corresponding, in kinaesthesia, to the one that is current when said movement has begun to be perceived by the person and/or, in stataesthesia, to the end-of-movement parameter that the person considers that he has reproduced, a step of calculating an absolute error corresponding, in kinaesthesia, to the difference between the starting target value of the movement and the estimated value of the start of perception of the movement by the person and/or, in stataesthesia, to the absolute difference between the target end-of-movement value imposed and the value estimated by the person for the end-of-movement reproduced, a repetition of these steps according to a predetermined number having been provided, for the same target value of the pivoting parameter, a step of calculating a variable error for each estimated value during repetitions, this variable error taking account of the variations in the absolute errors recording during repetitions, characterised in that the variable error Ev for a given absolute error Ea is calculated according to the equation:

$$Ev = \sqrt{(Ea - Moy_{Ea})^2}$$

with $Moy_{Ea}$ being a value that is a function of the absolute errors of all the repetitions and in that a proprioceptive score $S_p$ is calculated representing the proprioceptive status of the person tested from the absolute and variable errors, said score being defined by $$S_p = Med_{Ea} + Moy_{Ev}$$

where $Med_{Ea}$ is the averaged value of the absolute errors of the repetitions and $Moy_{Ev}$ is the averaged value of the variable errors of the repetitions, the proprioceptive scores of the person tested thus obtained being associated with an assessment time for use as a reference when the person tested is monitored or when the person tested is compared with at least one other person.

The technical effect is the obtaining of a method for the effective quantification of the proprioception of a person by means of a proprioceptive score. Through its calculation, taking account of the averaged absolute and variable values, a proprioceptive score is perfectly representative of the proprioception of the joint and can be interpreted on the assessment site, even by a non-specialist. This is because, taking account both of absolute errors and variable errors specifically averaged for the values, of the movement parameter measured for calculating the proprioceptive score reduces the magnitude of false measurements in the calculation, and hence a more reliable proprioceptive score is obtained.

Thus a more rapid and sure assessment of the proprioception of a person is obtained, along with facilitation of the monitoring of his proprioceptive status over time or comparing his status with the proprioceptive status of at least one other person, or by previous status of the said person.

Advantageously, $Moy_{Ea}$, the value that is a function of the absolute errors, is the mean of the errors or the median of the errors, while the averaged value of the variable errors is the mean of said errors. The use of the median of the absolute errors makes it possible not to take account of the extreme measurements in all the measurements of the repetitions, extreme measurements that could falsify the calculation of the proprioceptive score.

Advantageously, in stataesthesia, the proprioceptive scores are established for different target values of movement parameter.

Advantageously, the joint is a joint of a limb and the movement parameter is a pivot angle of said joint.

Advantageously, a global proprioceptive score is calculated that is at least a function of the proprioceptive score obtained in stataesthesia and the proprioceptive score obtained in kinaesthesia.

Advantageously, the proprioceptive scores of several persons with a similar profile are grouped together in order to give a proprioceptive score representative of the group, at least two groups of persons thus being formed, a linear regression being applied to said at least two proprioceptive scores each representative of a respective group, the position of the proprioceptive score of a new person tested with respect to a straight line obtained by the linear regression enabling it to be classified in one of the at least two groups.

According to a second aspect, the invention concerns an apparatus for assessing the proprioceptive status of at least one joint of a person being tested, said apparatus functioning in accordance with a method according to the above, said apparatus having a chair, at least two movable parts articulated on each other and means of driving at least one movable part, characterised in that each movable part has its own drive means, the means of driving the first movable part allowing a pivoting of the top part of the first movable part, the second movable part being connected to the bottom part of the first movable part, the means of driving the second movable part allowing a pivoting of the second movable part with respect to the first movable part, means of determining the pivot angle for each of the first and second parts being provided.

Such apparatus makes it possible to measure stataesthesia and/or kinaesthesia, for example, the two leg joints, that is to say the ankle and the knee, and advantageously for both legs.

Advantageously, the apparatus is an apparatus for assessing the proprioceptive status of at least one joint of a leg of the person to be tested, the two movable parts being articulated on each other extending substantially along the leg, the first movable part extending substantially form the knee to the ankle, the second movable part extending substantially at the ankle of the person being tested and a top part of the first movable part being connected to a fixing piece secured to the chair of the apparatus.

Alternatively or cumulatively, the apparatus is an apparatus for assessing the proprioceptive status of at least one joint of an arm of the person to be tested, the two movable part being articulated on each other extending substantially along the arm, the first movable part extending substantially from the elbow to the wrist, the second movable part extending substantially at the elbow of the person being tested.

Advantageously, the apparatus is provided with at least one control button making it possible, when it is actuated by the person being tested, to indicate, in kinaesthesia, when he has perceived the movement of his leg or, in stataesthesia, when he considers that he has reproduced the movement. The control button is a sure and effective means for the signalling by the person being evaluated of an end of movement or an estimated start of movement.

Advantageously, the apparatus comprises means of displaying the proprioceptive status and, during a measurement in kinaesthesia, the target angle and the estimated angle or start of perception of the movement or, during a measurement in stataesthesia, the target end-of-movement angle imposed and the estimated end-of-movement angle reproduced by the person. This makes the measurements made by the apparatus more accessible both for the experimenter and for the person being tested or for auxiliary personnel.

Advantageously, the drive means are placed close to the respective pivot point of the first and second movable parts, the means of determining the pivot angle being associated with the drive means and in the form of a potentiometer integrated in each drive means, each first and second movable part having means for the removable locking of their respective pivoting. Thus it is possible to selectively assess a joint, that is to say a knee or the ankle.

Advantageously, the movable parts have at least one bar, the drive means being connected to a respective shaft and bearing assembly.

Advantageously, the first movable part has two telescopic bars, the two bars being able to be locked in position with respect to each other by removable connection means. This makes it possible to adapt the length of the first part to the length of the bottom part of the assessed leg of the patient and contributes to the exactitude of the measurements and to the comfort of the person.

Advantageously, the second movable part is in the form of a bar and has a footrest at its bottom end. This contributes to the comfort of the person being assessed seated in the chair, and reducing the weight of the chair when the bar is hollow.

Advantageously, the seat of the chair has a seat slope with a height with respect to the floor that is less for its rear portion compared with its front portion, the backrest of the chair having a height of 40 to 50 cm with an inclination of approximately 10° towards the rear. This affords easy access to the chair for the person being assessed who has to sit down in the chair without any trouble, when this person may be handicapped by an injury at the joint being assessed. The apparatus is thus adjustable to any anatomy and comfortable. In addition, advantageously, the apparatus has pivoting/articulation means enabling it to be foldable. Thus the apparatus is easily transportable and compact, offering simplicity of assembly, this being able to be done by only one experimenter.

The invention finally concerns an assembly formed by such an apparatus and a control unit, the apparatus comprising or being associated with the control unit having means of memorising the target angles, the estimated pivot angles, the joint motion direction and measured time of a perceived movement of a tested person joint, and means of memorising data of the person being tested during various proprioceptive assessment measurements as well as means of calculating a score representing the proprioceptive state of the person being tested.

Thus it is possible to obtain an interpretation of the immediate results on the proprioceptive status of the person tested on the assessment site, practically in real time. The database relating to the person tested or to other persons for the purpose of a comparison is also accessible on site. The assembly consisting of the chair and its control unit makes available to the experimenter a reliable and precise tool while being easy to use and rapid to implement and offering a directly interpretable result.

Particularly in association with the display means, the assessment data are collected in a simple and intuitive fashion and the experimenter can be guided at each step of the assessment, for example by means of display means producing an intuitive interface, indicating for example which joint to test, which angle or which speed of movement.

Other features, aims and advantages of the present invention will emerge from a reading of the following detailed description with regard to the accompanying drawings given by way of non-limitative examples and in which.

The present invention relates first of all to a method of assessing the proprioceptive status for at least one joint of a segment (such as a member or a limb or a neck) of a person being tested, this status being assessed at least in stataesthesia or in kinaesthesia, these two modes having been previously defined.

Proprioception is to be taken in the broad sense, which includes equilibrium and postural control from the aspect of the visual and vestibular systems, kinaesthesia and sense of position. A deficiency in proprioception necessarily has repercussions on the stability of the joints and therefore on the risk of trauma. An advantageous but non-limitative application of the present method would be for the prevention and prediction of injuries. A systematic assessment of proprioceptive status therefore makes it possible to optimise the establishment of the prophylactic/re-educational proprioceptive training programmes and thus to limit the costs due to the treatment of the possible injuries.

Thus the joint of the limb that is the subject of the assessment of proprioception may or may not be injured. When this joint is injured, the monitoring of the proprioceptive status over the period of convalescence advantageously serves to establish the reestablishment of the joint. Advantageously, when a joint, injured or not, is the subject of proprioceptive assessment, the corresponding joint of the other limb forming the same pair with the limb tested may also be assessed. Among other things, this makes it possible to relativise the results obtained for the joint tested by taking account of the proprioceptive characteristics that are particular to the person in general and not especially particular to the joint tested first.

This is because the periarticular elements, for example capsula, nyotendinous complex, and ligaments, are not the only structures that have an influence on the proprioception of a person; the plantar cutaneous sensors as exteroceptors also play a major role.

Non-limitatively, in the field of sports training, many uses of the method according to the invention are possible. It may thus be possible to optimise the performance of players, the precision of a sports action being correlated with the proprioceptive status of the joints involved during the action. The proprioceptive results obtained by the present method my thus serve as a basis for establishing training programmes for players in order to increase their proprioceptive qualities.

Other more general applications in the field of business, in particular concerning engineering or ergonomics, are also possible. They may apply in fields in which a person, through his work, must operate levers or pedals or perform various actions. These actions may be optimised in terms of amplitude or firmness once the proprioceptive status of the person has been taken into account.

Another possible application is the assessment of brain damage in a person, for example of the hemiplegia type. This is done by comparing the proprioceptive value of a joint on two limbs in the same pair of a person.

A method according to the present invention comprises a step of imposing a pivoting movement on at least one joint on a limb of the tested person being monitored. For example, for a leg, this joint may be the knee or the ankle or, for an arm, the shoulder, the elbow or the wrist. It is of course possible and advantageous to assess the proprioception of these joints successively. In general, it is also advantageous to successively test a pair of limbs, for example the legs or the arms, for the purpose of comparison.

During kinaesthesia, this step is followed by a step of signalling by the person being tested that the movement has been perceived. A step of measuring the value of a pivoting parameter corresponding to the one for which the movement has begun to be perceived by the person is then carried out, this value being referred to as the estimated value. This pivoting parameter is advantageously the pivoting angle. It may however be different, for example may be a height of movement of the limb being acted on, or a movement time for the joint from which it is possible to derive the value of the pivoting angle knowing the speed of movement. Account may also be taken of several movement parameters for the joint, particularly for a complex joint such as the shoulder.

This pivoting parameter perceived may be very different from the actual value of the pivoting parameter at the start of the movement or target value if the proprioceptive qualities of the person being assessed are weakened. This may be the case, for example, for non-sportspersons or a group of sportspersons for whom the limb tested is weakened.

During stataesthesia, the movement imposed is continued to a value of the predetermined imposed end-of-movement parameter, referred to as the target value. After this imposition step, a step of direct or indirect movement reproduction by the person is carried out. Direct reproduction means that the person himself makes the reproduction movement while he is aided mechanically during indirect reproduction. The latter is preferred. The measurement of the estimated value of the pivoting parameter corresponding to the end of movement that the person considers he has reproduced is then made.

A step is then carried out of calculating an absolute error corresponding in kinaesthesia to the absolute difference between the starting target value of the movement and the value estimated by the person perceiving the movement and in stataesthesia to the absolute difference between the imposed target end-of-movement angle and the angle estimated by the person of end of movement reproduced.

The method provides for a repetition of these steps according to a predetermined number, in stataesthesia for the same pivoting angle imposed. Advantageously, this number may be between 5 and 10, preferentially 8. Next this method may be repeated for various imposed pivoting parameters, for example for three different pivot angles.

A variable error Ev is then calculated for each value measured during repetitions, this variable error taking account of the absolute variations in the errors recorded during repetitions. This variable error Ev for a given absolute error Ea is calculated according to the equation:

$$Ev = \sqrt{(Ea - Moy_{Ea})^2}$$

with $Moy_{Ea}$ being a value that is a function of the absolute errors over a series of repetitions, this function value not necessarily being the arithmetic mean of the absolute errors.

A proprioceptive score $S_p$ is then calculated, representing the proprioceptive status of the person tested from the absolute and variable errors when reproducing joint angles (Spsta) and/or when detecting joint movement (Spkin), said score being defined by:

$$S_{psta} = Med_{Ea} + Moy_{Ev}$$

$$S_{pkin} = Med_{Ea} + Moy_{Ev}$$

$$S_{ptot} = S_{psta} + S_{pkin}$$

where $Med_{Ea}$ is the averaged value of the absolute errors of repetitions and $Moy_{Ev}$ is the averaged value of the variable errors of the repetitions, the proprioceptive scores of the person tested thus obtained being associated with an assessment date and then stored so as to serve as a reference when the person tested is monitored or during a comparison of the person tested with at least one other person.

It is then possible to assess the proprioceptive score of another joint of the limb already tested, for example the knee and then the ankle for the leg or the shoulder and then the elbow or the wrist for the arm. The opposite and other combinations are of course possible.

In stataesthesia, the proprioceptive scores can be established for different target values of movement parameter. The movement parameter is advantageously the pivot ankle of the joint. For example, as previously indicated, n repetitions can be carried out for x angles, n advantageously being around 8 and x around 3, which makes 24 tests per joint. The tests are randomised in order to avoid the presentation effect, that is to say in this case $$\frac{24!}{8!(24-3)!}$$

possibilities.

As previously indicated, the value that is a function of the absolute errors may be the arithmetic mean but this is not necessarily the case. The median of the absolute errors is preferred for this value that is a function of the absolute errors while the averaged value of the variable errors is advantageously the mean of said errors.

A non-limitative example of calculating the proprioceptive score $S_p$ will now be given, in the case where the movement parameter is the pivot angle of the joint, this angle being called respectively $\alpha_c$ for the target angle and $\alpha_e$ for the estimated angle.

The absolute value of the absolute error Ea of the estimated angle $\alpha_e$ with respect to the target angle $\alpha_c$ is calculated.

$$Ea = \sqrt{(\alpha_e - \alpha_c)^2}$$

The median of the absolute error $Med_{Ea}$ of the n repetitions for the same angle is then calculated. Calculation by the median is preferred to arithmetic mean since it is not affected by the extreme estimated values Ea in all the data of the n repetitions.

Next the variable error Ev is calculated. This error represents the absolute difference between the absolute error Ea and the arithmetic mean of the absolute error $Moy_E$, for each test, that is to say:

$$Ev = \sqrt{(Ea - Moy_{Ea})^2}$$

with, n advantageously being equal to 8, $$Moy_{Ea} = \frac{1}{n} \sum_{i=1}^{n} Ea_i$$

The mean of the variable error $Moy_{Ev}$ of the repetitions is then calculated:

$$Moy_{Ev} = \frac{1}{n} \sum_{i=1}^{n} Ev_i$$

Finally, the proprioceptive score $S_p$ per target angle and per joint is calculated as follows:

$$S_p = Med_{Ea} + Moy_{Ev}$$

It is possible to create a database comprising the proprioceptive scores of several persons with a similar profile. These scores or persons with a similar profile can be grouped together in order to give a proprioceptive score representative of the group. Advantageously, at least two groups of persons may be thus formed; in the example to come four groups will thus be created. A linear regression is applied to said at least two proprioceptive scores each representative of a respective group. The position of the proprioceptive score of a new person tested with respect to a straight line obtained by the linear regression then enables it to be classified in one of the at least two groups.

Figure 1:
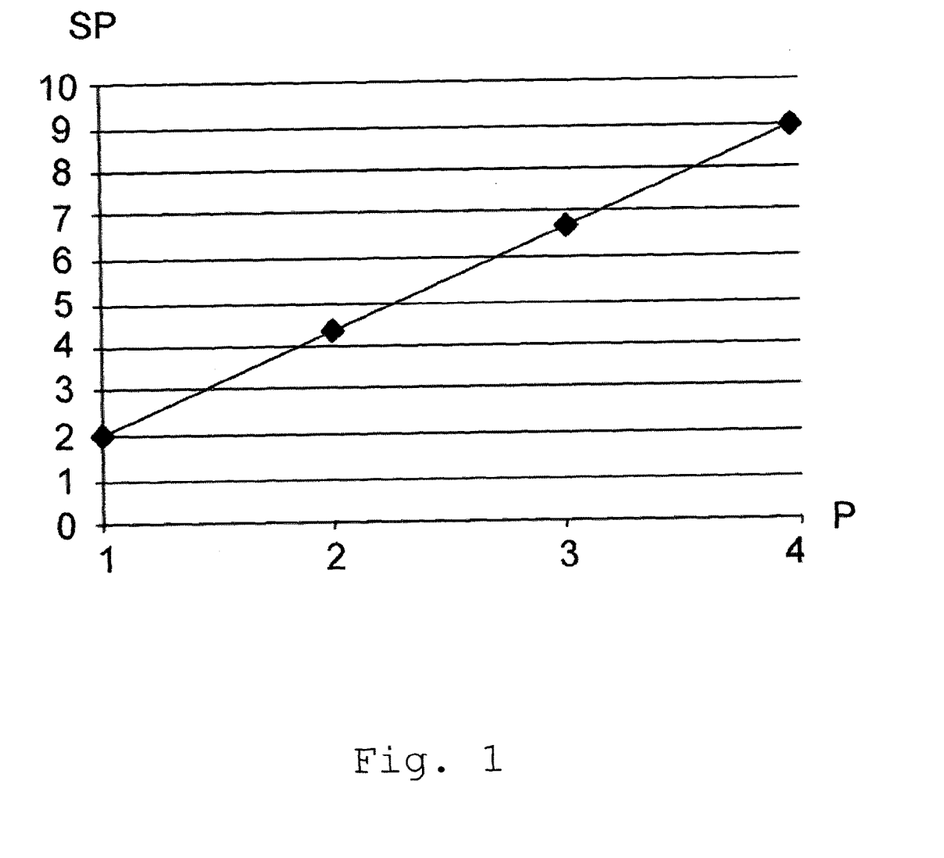
FIG. 1 is a curve illustrating, for the same pivot angle of a joint of a limb of persons being assessed, the proprioception coefficients of the various persons, forming a sample by groups representing the population assessed.

FIG. 1 shows the proprioceptive score curve Sp for the ankle of a leg for a given pivot angle, for four population groups P numbered from 1 to 4, this number not being limitative. The group 1 is formed from healthy professional sportsmen, group 2 from healthy amateur sportsmen, group 3 injured amateur sportsmen and group 4 healthy sedentary men. A reference proprioceptive score was established for each population group.

In the case illustrated in FIG. 1, the straight line obtained by linear regression is of equation:

$$y=2.34x-0.3$$

with a reliable trend ($R^2=0.99$) between the various population groups 1 to 4 and their respective proprioceptive scores.

Thus, for a proprioceptive score $S_p$, a good score is defined for $S_p \leq 4.3$, a moderate score for $4.3 < S_p < 6.7$ and a poor score for $S_p \geq 6.7$, which is not limitative but merely illustrative of the case shown in FIG. 1.

For various angles, it is possible to calculate a proprioceptive score for kinaesthesia and a score for stataesthesia. It is also possible to combine the two scores thus obtained in kinaesthesia and stataesthesia in order to obtain a global proprioceptive score. This global proprioceptive score may be at least the sum of the two proprioceptive scores thus obtained or the average of these two scores. Weighting coefficients may also be added to the scores.

Figure 2:
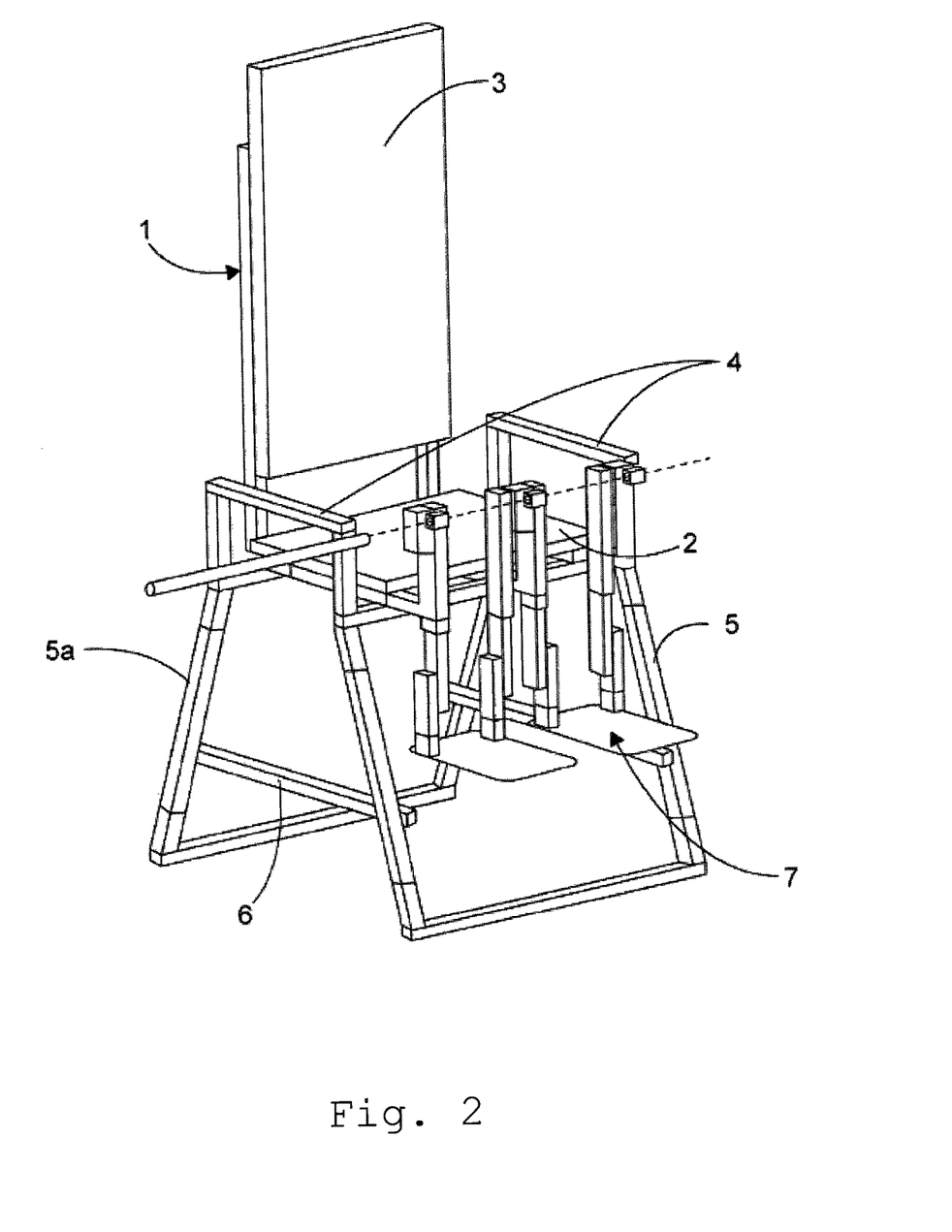
FIG. 2 is a schematic representation of a perspective view of an embodiment of a chair for the proprioceptive assessment of at least one joint of the leg of the person, this chair forming part of the assessment apparatus in accordance with the present invention.

FIG. 2 illustrates an embodiment of a chair 1 for the proprioceptive assessment of at least one leg of a person, this mode being in accordance with the present invention. This chair 1 comprises a seat 2, a backrest 3, armrests 4 and a support for its positioning on the floor.

Advantageously, the backrest 3 of the chair 1 has a height adjustable from 40 to 50 cm with an inclination of approximately 10° towards the rear. The distances between the seat 2 and the backrest 3 are also adjustable for adapting the morphology of each person while ensuring a standardised position.

The seat 2 is advantageously provided with a seat slope, that is to say a difference in height of approximately 2 cm for the rear of the seat 2 with respect to the front. All these characteristics make it possible to obtain a comfortable seating for the occupant of the seat 2 of the chair 1, enabling him to be entirely relaxed while causing no additional muscular fatigue other than that due to the taking of the measurements.

The support of the chair 1 is advantageously composed, at the front and rear of the chair 1, of a frame 5, 5a. Each frame 5, 5a is flat, empty inside and forming only its contour and delimiting a rectangular or square shape, one side of which rests on the floor forming a foot. Its top side is situated against the bottom face of the seat 2, advantageously respectively against the front side of the seat 2 for the front frame 5 or the rear side for the rear frame 5a.

The frames 5, 5a are inclined in opposite directions with respect to each other, towards the front of the chair 1 for the front frame 5 and towards the rear of the chair 1 for the rear frame 5a. On each side of the chair 1, a respective crossmember 6 connects each vertical side of the front frame 5 to the opposite side of the rear frame 5a, in their bottom or middle portion. These crossmembers 6 serve to ensure the stability of the chair 1 by making the front 5 and rear 5a frames integral.

Advantageously, the chair 1 is foldable. In one embodiment, it is the frames 5 and 5a that can be folded one towards the other while being articulated on the front side or respectively rear side of the seat 2 by hinges. The crossmember 6 can also be articulated, for example at the middle or on one of the ends, in order to be folded. The framework of the chair 1 is also lightweight in order to be transported more easily. The chair 1 can thus be transported easily, for example in a light vehicle.

The chair 1 comprises a device 7 for pivoting and measuring the pivoting of the leg joint the proprioceptive score of which it is wished to assess. This device 7 is symmetrical and can be adapted to both legs so that it is possible to assess the proprioceptive score of the two legs, this advantageously being done non-simultaneously. The framework of the chair 1 and also the device 7 are advantageously produced with hollow bars with aluminium square cross sections.

Figure 3:
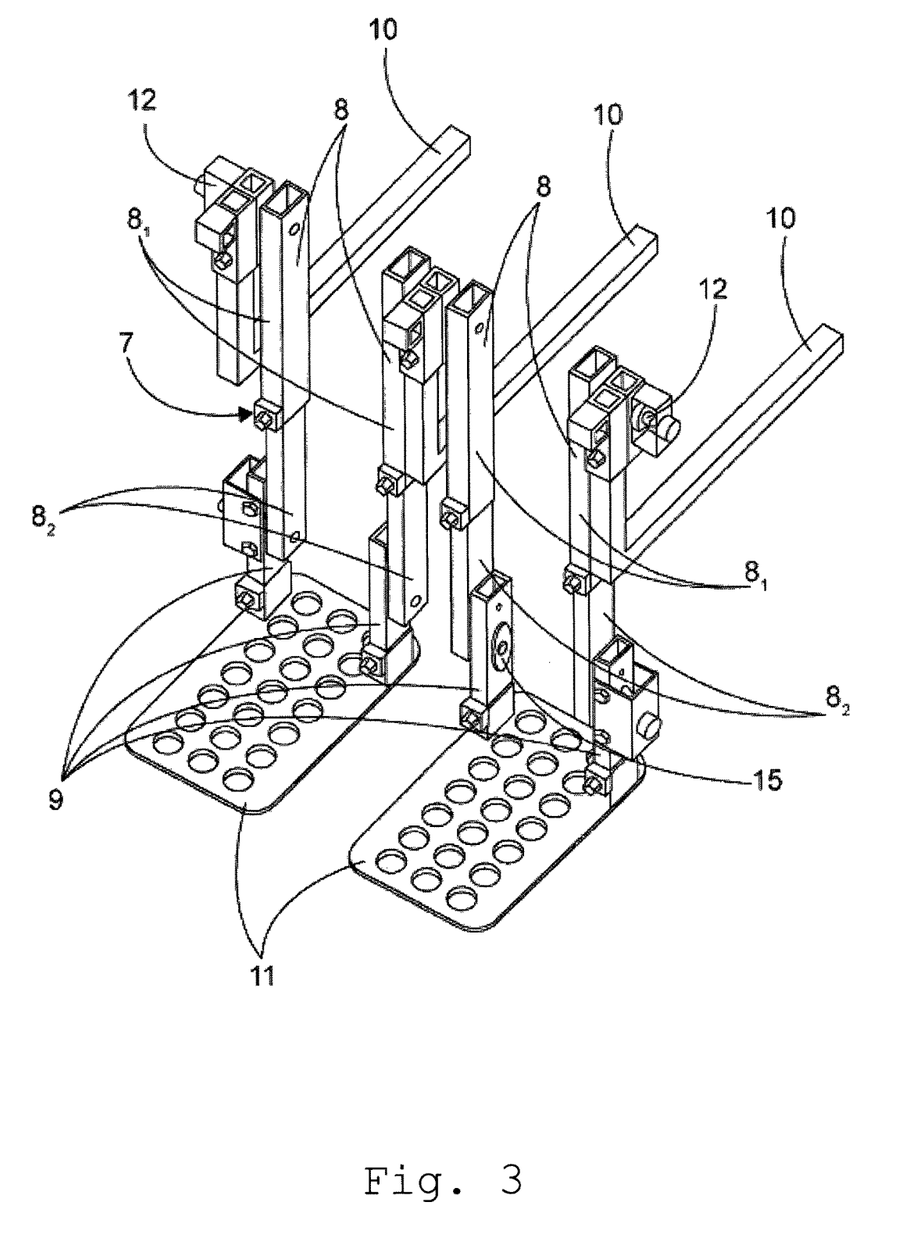
FIG. 3 is a schematic representation of an enlarged view in perspective of the device for pivoting a joint of the leg and then measuring this pivoting, forming part of the chair shown in FIG. 2.
Figure 4:
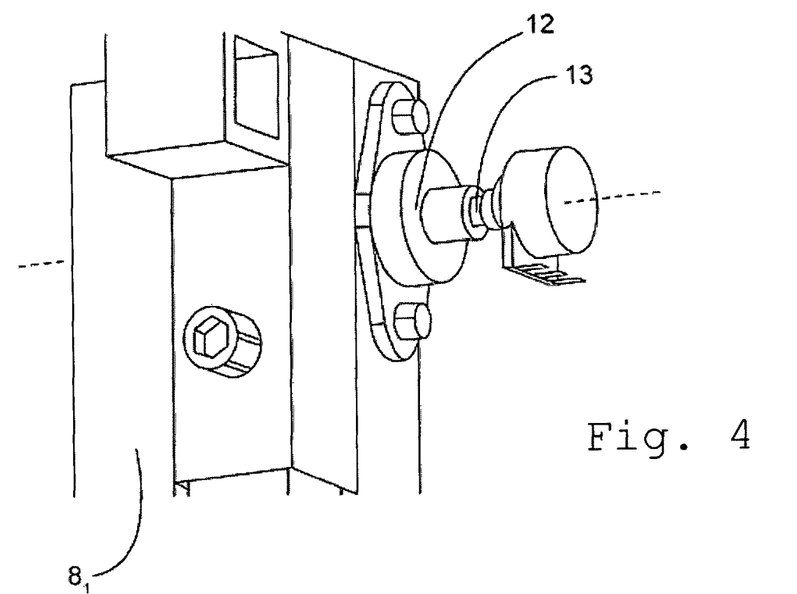
FIG. 4 is a schematic representation of an enlarged view in perspective of a part of the pivoting device shown in FIG. 3.

FIGS. 3 and 4 show at least partially the device 7 for pivoting and measuring the pivoting of a leg joint of the person seated in the chair.

With regard to FIG. 3, the pivoting device 7 has, for each leg, two movable parts 8 and 9 articulated on each other and extending substantially along the leg. The first movable part 8 extends substantially from the knee to the ankle, the top part of the first movable part 8 being connected to a fixing piece 10 secured to the chair of the apparatus. The fixing piece 10 is advantageously in the form of an angle bracket with a first arm of the angle bracket being integrated under the seat of the chair extending parallel to the thigh of the seated person. The other arm, perpendicular to the first, extends along a portion of the length of the first movable part 8.

The first movable part 8 is advantageously in the form of two telescopic bars $8_1$ and $8_2$ able to slide one in the other. The length of the first movable part 8 is thus adjustable and can therefore be adapted to various leg lengths between knee and ankle of the person seated in the chair. In the embodiment shown in FIG. 3, it is the bottom telescopic bar $8_2$ that enters the top telescopic bar $8_1$.

The bottom telescope bar $8_2$ thus has a smaller cross section that the top telescopic bar $8_1$, for example respectively cross sections of 25 and 30 mm, which makes it possible to modulate the length of the first movable part 8 by fitting together the two bars $8_1$, $8_2$ according to the length of the leg of the patient. The two bars $8_1$ and $8_2$ are locked in position with respect to each other by removable securing means, advantageously manually tightened screws, in particular with a resin head.

The second movable part 9, advantageously also in the form of a bar, extends substantially level with the ankle of the person being assessed and is connected to the bottom part of the first removable part 8, that is to say to the bottom telescopic bar $8_2$, advantageously in its middle longitudinal portion. The bottom end of the second movable part 9 carries a footrest 11.

Drive means 12, 15 specific for each movable part 8 or 9 are provided, advantageously placed close to the respective pivot point. The drive means 12 of the first movable part 8, also visible in FIG. 4, allow pivoting of the top part of the first movable part 8, that is to say the top part of the top telescopic bar $8_1$, with respect to the fixing piece 10. The drive means 15 of the second movable part 9 enable the middle longitudinal portion of the second part 9 to make a pivoting of the second part 9 with respect to the bottom part of the first movable part 8, that is to say the bottom part of the bottom telescopic bar $8_2$. Means 13, visible in FIG. 4, of determining the pivot angle for each of the first and second parts 8, 9 are also provided.

Use of the drive means 12, 15 avoids an experimenter having to manually mobilise the assessed leg of the person by various manipulations on the different movable parts 8, 9 of the device 7, these manipulations being able to involve positions that are both uncomfortable and tiring for the person. The use of the drive means 12, 15 thereby reduces to a single person the number of experimenters necessary for assessing proprioceptive status with the apparatus according to the present invention.

In stataesthesia, the use of drive means 12, 15 or the pivoting movements of the joint being tested makes it possible to optimise the precision of the target value of the angle of the movement imposed while enabling the target value of the angle to remain perfectly constant during the time of stoppage of the pivoting movement imposed before the beginning of the movement which is reproduced, this stoppage time serving for the memorisation of the target value by the person being evaluated.

In addition, in kinaesthesia, the drive means offer the possibility of precisely assessing the value the target angle for detection of the passive movement by the person being assessed, while making it possible to mobilise the movable parts 8, 9 at speeds of less than 0.5°/s, which is impossible to obtain manually.

The drive means 12, 15 are advantageously servo-motor driven and comprise at least a jack. They are as quiet as possible so as to avoid any indication of start of movement to the person being assessed. This person is also blindfolded in order not to see the movement of his joint. These drive means 12, 15 form, advantageously, angular rotation means.

At the point of pivoting of the first movable part 8 with respect to the fixing piece 10 and at the pivot point of the second movable part 9 with respect to the first movable part 8, the pivoting takes place by means of a shaft in a bearing, the drive means being connected to the shaft. The bearings and their respective shafts are advantageously arranged so that the pivoting of each shaft in its respective bearing is also as quiet as possible.

Each pivot point can be locked and unlocked rapidly by removable locking means, advantageously a system of pins, so that a joint of the leg is assessed without involving the other joint. Advantageously, as also shown in FIG. 4, the measurement of the pivot angle is made, as a determination means, by a potentiometer 13 measuring a voltage wish is transmitted as an analogue signal to a control unit. This unit can be associated with the chair while being integrated therein advantageously removably, or being placed at a distance from said chair, for example in the form of a computer, in particular a portable computer, with means of transmission between the chair and the control unit.

Data can be acquired by recording the analogue signal measured by potentiometers 13 by means of an analogue to digital conversion and sampling card, which allows both the supply of the potentiometers 13 in continuous supply and the recording of the data by the control unit, advantageously, a portable computer, via a USB bus.

The control unit can advantageously have means of storing the target angle values and the estimated values of the pivot angles. The estimated angles are angle values that are stored according to a signal given by the person being assessed. This can be done by the actuation of a control button by the person, this button advantageously being placed on the armrest 4 of the chair 1 shown in FIG. 1.

The control unit also has means of storing the data of the person being assessed during various measurements, for example for the n pivoting repetitions. Finally, the control unit has means of calculating a score representing the proprioceptive state of the person assessed, according to a computing algorithm, this score being able to be a global score comprising at least the proprioceptive scores obtained in stataesthesia and/or in kinaesthesia.

The control unit or the chair can be provided with means of displaying various data relating to proprioception, in particular pivot angle values and the proprioceptive score.

As the assessment apparatus according to the present invention was intended to be used by a wide range of operators, for example medical personnel such as doctors, nurses, physiotherapists and carers but also non-medical personnel in particular from among sports staff, such as trainers, physical preparation staff or recruiters, the presentation of the display means must allow intuitive use of the proprioceptive assessment accessible to all.

The proprioceptive score is displayed as clearly as possible in relation to a gauge or graduations representing good, moderate and poor scores, where applicable with complementary data such as the pivot angles measured. In compliance with standards in respect of ergonomics, these various items of information may be organised by order of importance from left to right and from top to bottom.

Figure 5:
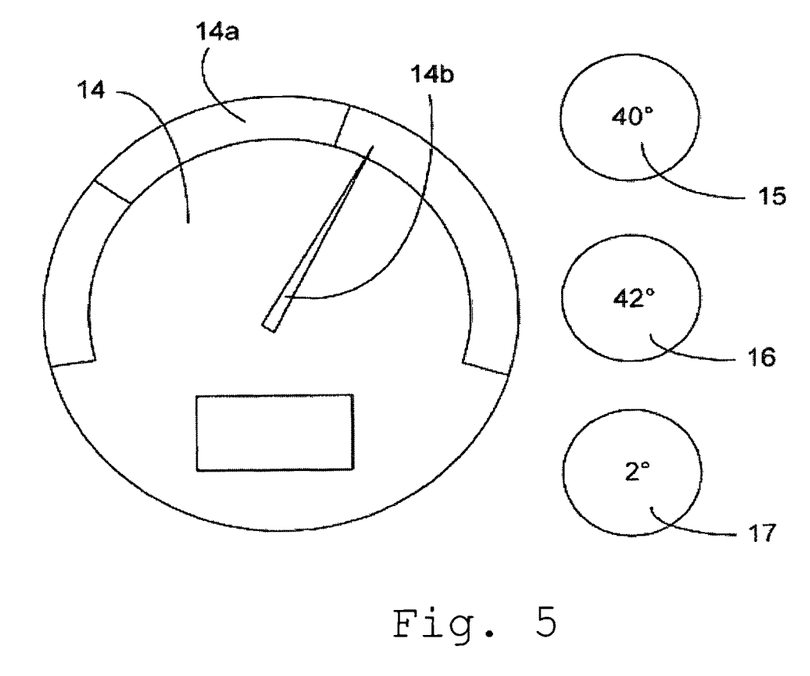
FIG. 5 is a schematic representation of a front view of dials used for displaying proprioceptive data measured.

In one embodiment of the display means, these means comprise a dial 14 having an indication means such as a needle 14b pointing to the proprioception score on a gauge 14a presenting easily recognisable areas of good, moderate and poor proprioception scores, these areas being for example of different colours and being also able to be a number different from three. One or more additional dials may also be provided, for example a target result dial 15 indicating the target angle, here 40°, an estimated result dial 16 indicating the estimated angle, here 42°, and an absolute error dial 17 indicating the absolute error, here 2°.

In addition, the display means may serve for guiding the experimenter at each assessment step, by indicating for example which joint to test, which target angle or which movement speed, a supplementary display means then being provided. The display means may also serve for controlling the drive means of the apparatus.

It is possible to store in the control unit a normative database that interprets the proprioceptive score of the person assessed according for example to his sex, his age, his sports practice and/or his medical antecedents, etc. This database is advantageously supplemented and updated by the proprioceptive scores of new persons as they are assessed.

Such a database makes it possible not only to compare the results of the person assessed with respect to a norm, for example a group of persons assessed having a similar profile but also to compare the results of the person being assessed during several periods of time. The database also makes it possible to monitor the efficacy of neuromuscular training or the reestablishment of proprioceptive functions of a given person, for example following an injury to the joint assessed. Finally, this database may make it possible, in the medium and long terms, to establish scores that will constitute an international standard for the measurement of proprioception.

The control unit may also, by display means, present graphs based on the stored data representing an assessed person or group for prophylactic proprioceptive assessment. These graphs, advantageously with legends and comments, assist the operators in interpreting the results and communicating them didactically to the assessed persons or to their management.

If the apparatus according to the invention has been described above for assessing the proprioceptive score of a leg joint, this apparatus can also be modified in an obvious manner to serve for assessing an arm joint, the movable parts extending along the arm, the movable part corresponding to the top part of the arm being connected to a bracket secured to the chair, the direction of pivoting of the movable parts then corresponding to the direction of pivoting of the joint of the arm being assessed.

Figure 6:
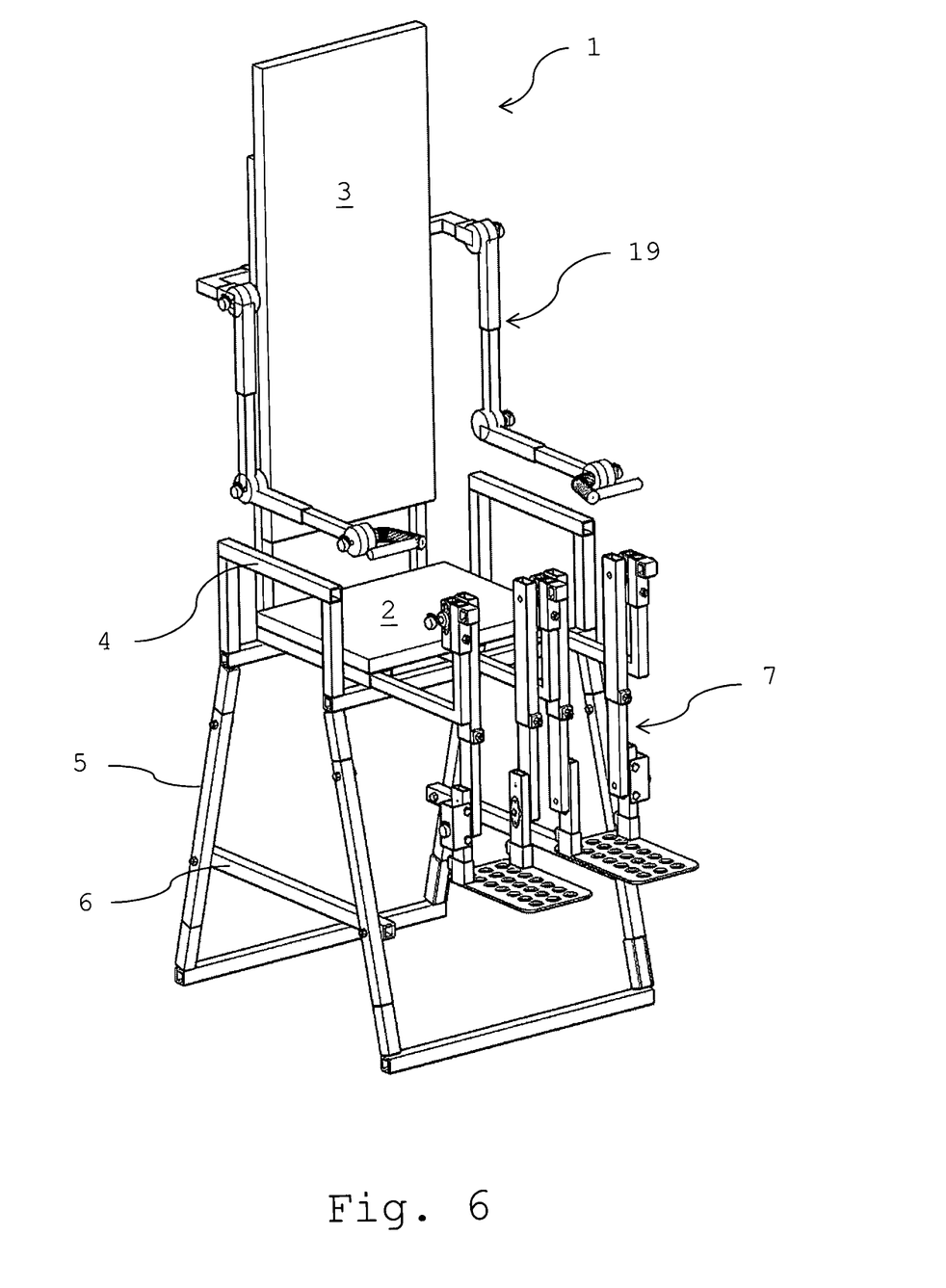
FIG. 6 is a schematic representation of a perspective view of an embodiment of a chair for the proprioceptive assessment of at least one joint of the arm or of the leg of the person, this chair forming part of the assessment apparatus in accordance with the invention.

For example, FIG. 6 illustrates an embodiment of a chair 1 for the proprioceptive assessment of at least one leg or one arm of a person. As in the embodiment of FIG. 2, this chair 1 is advantageously foldable and comprises a seat 2, a backrest 3, armrests 4, a frame 5, and cross-members 6. However, this chair 1 comprises, not only, a device 7 dedicated to the legs but, also, a device 19 dedicated to the proprioceptive assessment of at least one arm. This device 19 is symmetrical and can be adapted to both arms so that it is possible to assess the proprioceptive score of the two arms, this advantageously being done non-simultaneously.

Figure 7:
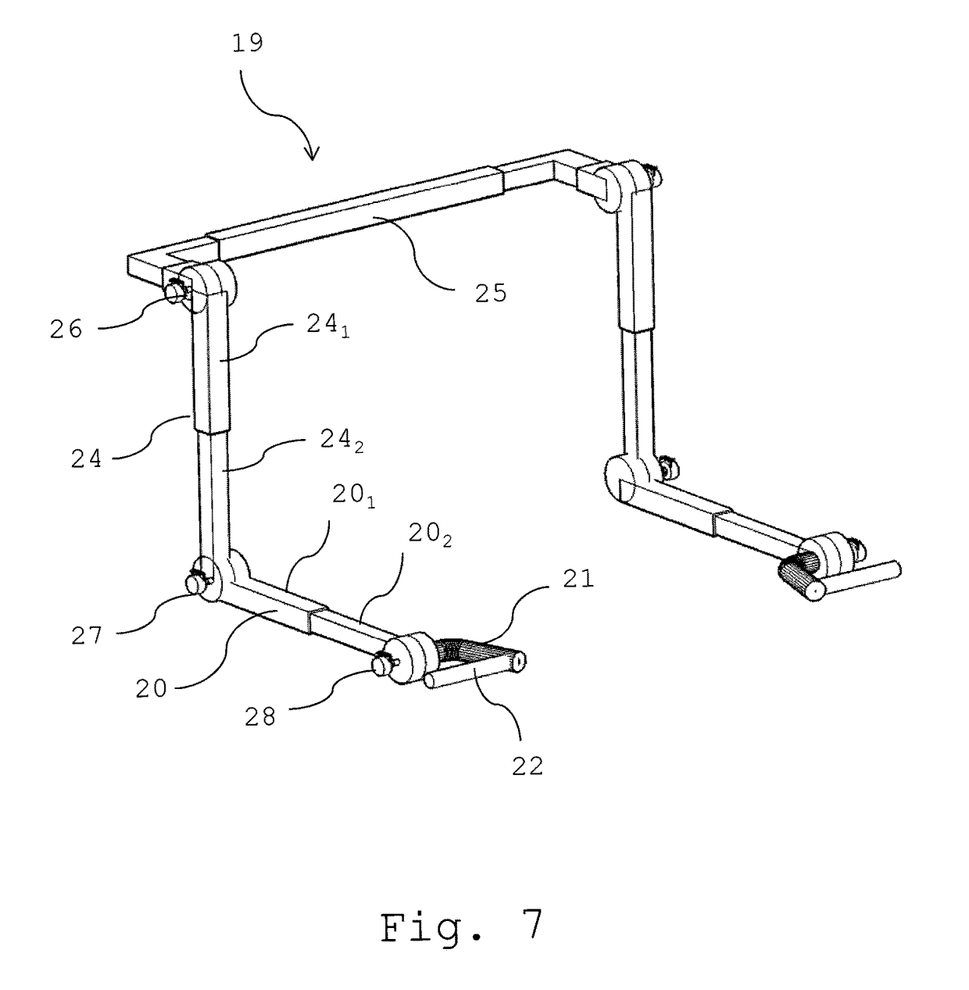
FIG. 7 is a schematic representation of an enlarged view in perspective of the device for pivoting a joint of the arm and then measuring this pivoting, forming part of the chair shown in FIG. 6.

FIG. 7 shows the device 19 for pivoting and measuring the pivoting of an arm joint of the person seated in the chair.

The device 19 is advantageously produced with hollow bars with aluminium square cross sections. It has, for each arm, three movable parts 20, 21 and 22 articulated on each other and extending substantially along the arm.

The first movable part 20 extends substantially from the elbow to the wrist. The first movable part 20 is advantageously in the form of two telescopic bars $20_1$ and $20_2$ able to slide one in the other. The length of the first movable part 20 is thus adjustable and can therefore be adapted to various arm lengths between the elbow and the wrist of the person seated in the chair. The two bars $20_1$ and $20_2$ are locked in position with respect to each other by removable securing means, for example, manually tightened screws.

The second movable part 21, extends substantially with the wrist of the person being assessed and is connected to the bottom part of the first removable part 20, that is to say to the bottom telescopic bar $20_2$. The bottom end of the second movable part 21 carries a handle 22.

The third movable part 24 extends substantially from the shoulder to the elbow. It is advantageously in the form of two telescopic bars $24_1$ and $24_2$ able to slide one in the other. The length of the third movable part 24 is thus adjustable and can therefore be adapted to various arm lengths between the shoulder and the wrist of the person seated in the chair. The two bars $24_1$ and $24_2$ are locked in position with respect to each other by removable securing means, for example, manually tightened screws.

The top part of the third movable part 24 is connected to a fixing piece 25 secured to the chair 1 of the apparatus. The fixing piece 25 is advantageously in the form of a transversal bar being integral with the backrest 3 of the chair.

Drive means 26, 27, 28 specific for each movable part 20, 21, 24 are provided, advantageously placed close to the respective pivot point. Preferentially, the drive means are servo-motor driven.

The combination of the assessment method and apparatus according to the present invention makes available to personnel not specifically qualified a reliable and precise tool while being easy to use, rapid to implement and offering a directly interpretable result.

Compared with a clinical measurement of proprioception that relates to observation, which makes it subjective and dependent on the experience of the skilled personnel doing it, the assessment according to the method and the apparatus in accordance with the present invention is objective, quantifiable, reproducible and standardised. These objective data inform clearly and precisely about the requirements, progress and results of one or more assessed persons.

The invention claimed is:

1. A method of assessing the proprioceptive status for at least one joint of a person being tested, this status being assessed in stataesthesia and/or in kinaesthesia, comprising:
   providing an apparatus for assessing said proprioceptive status,
   imposing a pivoting movement on the joint of the person being tested, which is at least one of (i) in kinaesthesia, followed by obtaining from the person an indication that the movement has been perceived or stopped, and (ii) in stataesthesia, after stopping the movement imposed when a predetermined target value of at least one parameter of the movement has been reached, followed by obtaining reproduction of the movement by the person,
   measuring an estimated value of the parameter of the movement corresponding to at least one of, (i) in kinaesthesia, the parameter that is current when said movement has begun to be perceived by the person and (ii) in stataesthesia, the end-of-movement parameter that the person considers that the person has reproduced,
   calculating an absolute error corresponding to at least one of, (i) in kinaesthesia, the difference between the starting target value of the movement and the estimated value of the start of perception of the movement by the person, and (ii) in stataesthesia, the absolute difference between the target end-of-movement value imposed and the value estimated by the person for the end-of-movement reproduced,
   carrying out repetitions of the imposing, measuring and calculating according to a predetermined number having been provided, for the same target value of the pivoting parameter,
   calculating a variable error for each estimated value during repetitions, this variable error taking into account the variations in the absolute errors recording during repetitions,
   wherein the variable error Ev for a given absolute error Ea is calculated according to the equation:

$$Ev=\sqrt{(Ea-Moy_{Ea})^2}$$

with $Moy_{Ea}$ being a value that is a function of the absolute errors of all the repetitions and wherein a proprioceptive score $S_p$ is calculated representing the proprioceptive status of the person tested from the absolute and variable errors, said score being defined by $$S=Med_{Ea}+Moy_{Ev}$$

where $Med_{Ea}$ is the averaged value of the absolute errors of the repetitions and $Moy_{Ev}$ is the averaged value of the variable errors of the repetitions, the proprioceptive scores of the person tested thus obtained being associated with an assessment time for use as a reference when the person tested is monitored or when the person tested is compared with at least one other person.

2. The method according to claim 1, wherein $Moy_{Ea}$ is the mean of the errors or the median of the errors while the average value of the variable errors is the mean of said errors.

3. The method according to claim 1, wherein, in stataesthesia, the proprioceptive scores are established for various target values of movement parameters.

4. The method according to claim 1, wherein the joint is a joint of a limb and the movement parameter is a pivot angle of said joint.

5. The method according to claim 1, wherein a global proprioceptive score is calculated that is at least a function of the proprioceptive score obtained in stataesthesia and the proprioceptive score obtained in kinaesthesia.

6. The method according to claim 1, wherein the proprioceptive scores Sp of several persons with a similar profile are grouped together in order to give a proprioceptive score representative of the group, at least two groups of persons thus being formed, a linear regression being applied to said at least two proprioceptive scores each representative of a respective group, the position of the proprioceptive score of a new person tested with respect to a straight line obtained by the linear regression enabling it to be classified in one of the at least two groups.

7. An apparatus for assessing the proprioceptive status of at least one joint of a person being tested,
said apparatus comprising a chair, at least first and second movable parts articulated on each other,
wherein each of the first and second movable parts has its own drive means, the drive means of the first movable part allowing a pivoting of the top part of the first movable part, the second movable part being connected to the bottom part of the first movable part, the drive means of the second movable part allowing a pivoting of the second movable part with respect to the first movable part, and
wherein the apparatus has means of determining the pivot angle for each of the first and second parts,
wherein the apparatus is configured to implement a method of assessing the proprioceptive status for at least one joint of a person being tested, this status being assessed in stataesthesia and/or in kinaesthesia, comprising:
providing an apparatus for assessing said proprioceptive status,
imposing a pivoting movement on the joint of the person being tested, which is at least one of (i) in kinaesthesia, followed by obtaining from the person an indication that the movement has been perceived or stopped, and (ii) in stataesthesia, after stopping the movement imposed when a predetermined target value of at least one parameter of the movement has been reached, followed by obtaining reproduction of the movement by the person,
measuring an estimated value of the parameter of the movement corresponding to at least one of, (i) in kinaesthesia, the parameter that is current when said movement has begun to be perceived by the person and (ii) in stataesthesia, the end-of-movement parameter that the person considers that the person has reproduced,
calculating an absolute error corresponding to at least one of, (i) in kinaesthesia, the difference between the starting target value of the movement and the estimated value of the start of perception of the movement by the person, and (ii) in stataesthesia, the absolute difference between the target end-of-movement value imposed and the value estimated by person for the end-of-movement reproduced,
carrying out repetitions of the imposing, measuring and calculating according to a predetermined number having been provided, for the same target value of the pivoting parameter,
calculating a variable error for each estimated value during repetitions, this variable error taking into account the variations in the absolute errors recording during repetitions,
wherein the variable error Ev for a given absolute error Ea is calculated according to the equation:

$$Ev=\sqrt{(Ea-MOY_{Ea})^2}$$

with $Moy_{Ea}$ being a value that is a function of the absolute errors of all the repetitions and wherein a proprioceptive score $S_p$ is calculated representing the proprioceptive status of the person tested from the absolute and variable errors, said score being defined by $$S_p = Med_{Ea} + Moy_{Ev}$$

where $Med_{Ea}$ is the averaged value of the absolute errors of the repetitions and $Moy_{Ev}$ is the averaged value of the variable errors of the repetitions, the proprioceptive scores of the person tested thus obtained being associated with an assessment time for use as a reference when the person tested is monitored or when the person tested is compared with at least one other person.

8. The apparatus according to claim 7, which is provided with at least one control button making it possible, when the control button is actuated by the person being tested, to indicate, in kinaesthesia, when the person has perceived the movement of his leg or, in stataesthesia, when the person considers that the person has reproduced the movement.

9. The apparatus according to claim 7, which comprises a visual display displaying the proprioceptive status and, during a measurement in kinaesthesia, the target angle and the estimated angle of start of perception of the movement or, during a measurement in stataesthesia, of the end-of-movement target angle imposed and the estimated end-of-movement angle reproduced by the person.

10. The apparatus according to claim 7, wherein the drive means are placed close to the respective pivot points of the first and second movable parts, the means of determining the pivot angle being associated with the drive means and in the form of a potentiometer integrated in each drive means.

11. The apparatus according to claim 7, wherein the drive means are connected to a respective shaft and bearing assembly, each of the first and second movable parts being adapted to have their respective pivoting locked.

12. The apparatus according to claim 7, wherein the first movable part has two telescopic bars, said two telescopic bars being able to be locked in position with respect to each other.

13. The apparatus according to claim 7, wherein a seat of the chair has a seat slope with a height with respect to the ground that is lower for a rear portion of the seat compared with a front portion of the seat, a backrest of the chair having a height of 40 to 50 cm with an inclination of approximately 10° towards the rear, the apparatus being articulated enabling it to be foldable.

14. The apparatus according to claim 7, which is an apparatus for assessing the proprioceptive status of at least one joint of a leg of the person to be tested, the first and second movable parts being articulated on each other extending substantially along the leg, the first movable part extending substantially form the knee to the ankle, the second movable part extending substantially at the ankle of the person being tested and a top part of the first movable part being connected to a fixing piece secured to the chair of the apparatus.

15. The apparatus according to claim 7, which is an apparatus for assessing the proprioceptive status of at least one joint of an arm of the person to be tested, the first and second movable part being articulated on each other extending substantially along the arm, the first movable part extending substantially from the elbow to the wrist, the second movable part extending substantially at the elbow of the person being tested.

16. An assembly formed by the apparatus according to claim 7 and a control unit, the apparatus comprising or being associated with the control unit which is capable of storing the target angles and estimated pivot angles and storing data on the person tested during various proprioceptive assessment measurements as well as calculating a score representing the proprioceptive state of the person tested.

17. The apparatus according to claim 8, which comprises a visual display displaying the proprioceptive status and, during a measurement in kinaesthesia, the target angle and the estimated angle of start of perception of the movement or, during a measurement in stataesthesia, of the end-of-movement target angle imposed and the estimated end-of-movement angle reproduced by the person.

18. The apparatus according to claim 17, wherein the drive means are placed close to the respective pivot points of the first and second movable parts, the means of determining the pivot angle being associated with the drive means and in the form of a potentiometer integrated in each drive means.

19. The apparatus according to claim 8, wherein the drive means are placed close to the respective pivot points of the first and second movable parts, the means of determining the pivot angle being associated with the drive means and in the form of a potentiometer integrated in each drive means.

20. The apparatus according to claim 9, wherein the drive means are placed close to the respective pivot points of the first and second movable parts, the means of determining the pivot angle being associated with the drive means and in the form of a potentiometer integrated in each drive means.

* * * * *